(12) United States Patent
Suzuki (10) Patent No.: US 8,194,981 B2
(45) Date of Patent: Jun. 5, 2012

(54) FLUORESCENT SIGNAL ANALYZING APPARATUS AND FLUORESCENT SIGNAL ANALYZING METHOD

(75) Inventor: Akemi Suzuki, Kokubunji (JP)

(73) Assignee: Olympus Corporation, Tokyo (JP)

( * ) Notice: Subject to any disclaimer, the term of this patent is extended or adjusted under 35 U.S.C. 154(b) by 455 days.

(21) Appl. No.: 12/486,058

(22) Filed: Jun. 17, 2009

(65) Prior Publication Data

US 2009/0252414 A1 Oct. 8, 2009

Related U.S. Application Data

(63) Continuation of application No. PCT/JP2008/050039, filed on Jan. 7, 2008.

(30) Foreign Application Priority Data

Jan. 16, 2007 (JP) ................. 2007-007280

(51) Int. Cl.
*G06K 9/00* (2006.01)
*G06K 9/46* (2006.01)
(52) U.S. Cl. ...................... 382/170; 382/190
(58) Field of Classification Search .............. 382/168, 382/190, 278, 170
See application file for complete search history.

(56) References Cited

U.S. PATENT DOCUMENTS

| | | | | |
|---|---|---|---|---|
| 7,400,396 | B2 * | 7/2008 | Watanabe et al. ............. | 356/317 |
| 2006/0256338 | A1 * | 11/2006 | Gratton et al. ................ | 356/417 |

FOREIGN PATENT DOCUMENTS

| | | |
|---|---|---|
| JP | 2001-258599 | 8/2001 |
| JP | 2006-292420 | 10/2006 |
| JP | 2006-350740 | 12/2006 |
| WO | WO 2004/072624 A1 | 8/2004 |

OTHER PUBLICATIONS

Wiseman, et al., "Two-photon Image Correlation Spectroscopy and Image Cross-Correlation Spectroscopy", Proceedings of the SPIE, The International Society for Optical Engineering SPIE-INT, 2001, pp. 279-286, vol. 4262.

Srivastava, M., et al., "Diffusion of Transferrin receptor clusters", Biophysical Chemistry, Dec. 14, 1998, pp. 201-211, vol. 75, No. 3.

Nohe, A., et al., "Dynamics of GPI-anchored proteins on the surface of living cells", Nanomedicine: Nanotechnology, Biology, and Medicine, Mar. 1, 2006, pp. 1-7, vol. 2, No. 1.

Srivastava, M, et al., "Image cross-correlation spectroscopy: A new experimental biophysical approach to measurement of slow diffusion of fluorescent molecules", Methods in Cell Science, Mar. 1996, pp. 47-54, vol. 18, No. 1.

Wiseman, Paul W. et al., "Image Correlation Spectroscopy. II. Optimization for Ultrasensitive Detection of Preexisting Platelet-Derived Growth Factor-β Receptor Oligomers on Intact Cells", Biophysical Journal (1999), vol. 76, pp. 963-977.

* cited by examiner

*Primary Examiner* — Daniel Mariam
(74) *Attorney, Agent, or Firm* — Scully, Scott, Murphy & Presser, P.C.

(57) ABSTRACT

A fluorescent signal analyzing apparatus includes an image input unit, a storage unit, an extracting unit, and an analyzing unit. At least one fluorescent image of a sample is input to the input unit. The storage unit stores data on the at least one fluorescent image input to the image input unit. The extracting unit extracts, for each of the fluorescent images, data on a fluorescence intensity in a desired region on the at least one fluorescent image from the data on the at least one fluorescent image stored in the storage unit. The analyzing unit calculates at least one of a correlation and a photon counting histogram for the desired region by use of the data on the fluorescence intensity.

19 Claims, 7 Drawing Sheets

| 1.21 | 1.22 | 1.18 | 1.2  | 1.19 | 1.18 | 1.2  | 1.22 |
|------|------|------|------|------|------|------|------|
| 1.18 | 1.2  | 1.19 | 1.2  | 1.22 | 1.19 | 1.18 | 1.2  |
| 1.19 | 1.22 | 1.18 | 1.18 | 1.2  | 1.2  | 1.22 | 1.19 |
| 1.19 | 1.18 | 1.2  | 1.19 | 1.22 | 1.18 | 1.18 | 1.2  |
| 1.17 | 1.21 | 1.2  | 1.22 | 1.19 | 1.18 | 1.2  | 1.19 |
| 1.16 | 1.2  | 1.22 | 1.19 | 1.18 | 1.2  | 1.22 | 1.18 |
| 1.21 | 1.18 | 1.22 | 1.18 | 1.19 | 1.2  | 1.22 | 1.19 |
| 1.21 | 1.2  | 1.22 | 1.19 | 1.22 | 1.18 | 1.18 | 1.2  |

FLUORESCENT SIGNAL ANALYZING APPARATUS AND FLUORESCENT SIGNAL ANALYZING METHOD

CROSS-REFERENCE TO RELATED APPLICATIONS

This is a Continuation Application of PCT Application No. PCT/JP2008/050039, filed Jan. 7, 2008, which was published under PCT Article 21(2) in Japanese.

This application is based upon and claims the benefit of priority from prior Japanese Patent Application No. 2007-007280, filed Jan. 16, 2007, the entire contents of which are incorporated herein by reference.

BACKGROUND OF THE INVENTION

1. Field of the Invention

The present invention relates to an optical signal analyzing apparatus and an optical signal analyzing method.

2. Description of the Related Art

An optical signal analyzing method using LSM image data has heretofore been disclosed in "Image Correlation Spectroscopy. II. Optimization for Ultrasensitive Detection of Pre-existing Platelet-Derived Growth Factor-β Receptor Oligomers on Intace Cells.", Paul W. Wiseman and Nils o. Petersen, Biophysical Journal, Vol. 76, P 963, 1999. In this document, the LSM image data used for a correlation operation includes a single image. In this data, the integrated value of fluorescence intensities at different spatial positions is used to study correlativity associated with the difference of the spatial positions.

When the measured data is the integrated value of fluorescence intensities at different spatial positions as in the case of the conventional technique described above, information on fluctuations on a spatial axis is obtained, but information on fluctuations on a time axis is not obtained. It is therefore impossible to observe the behavior or interaction of living cells on the time axis. That is, the image of the fluorescence intensities at the spatial positions alone does not enable the observation of changes over time in, for example, reactions and interactions made in and out of the cells or signal transmission within the cells.

DISCLOSURE OF THE INVENTION

The present has been proposed in view of such circumstances, and is directed to provide a fluorescent signal analyzing apparatus and a fluorescent signal analyzing method that enable observation of changes over time.

A fluorescent signal analyzing apparatus according to the present invention includes an image input unit to which at least one fluorescent image of a sample is input, a storage unit to store data on the at least one fluorescent image input to the image input unit, an extracting unit to extract, for each of the fluorescent images, data on a fluorescence intensity in a desired region on the at least one fluorescent image from the data on the at least one fluorescent image stored in the storage unit, and an analyzing unit to calculate at least one of a correlation and a photon counting histogram for the desired region by use of the data on the fluorescence intensity.

DETAILED DESCRIPTION OF THE INVENTION

Hereinafter, embodiments of the present invention will be described with reference to the drawings.

<First Embodiment>

FCS/FCCS by Extracted Data for the Same Desired Region

The present embodiment provides a technique for an analysis by extracting data at the same spatial position from data for a plurality of fluorescent images of a sample.

Figure 1:
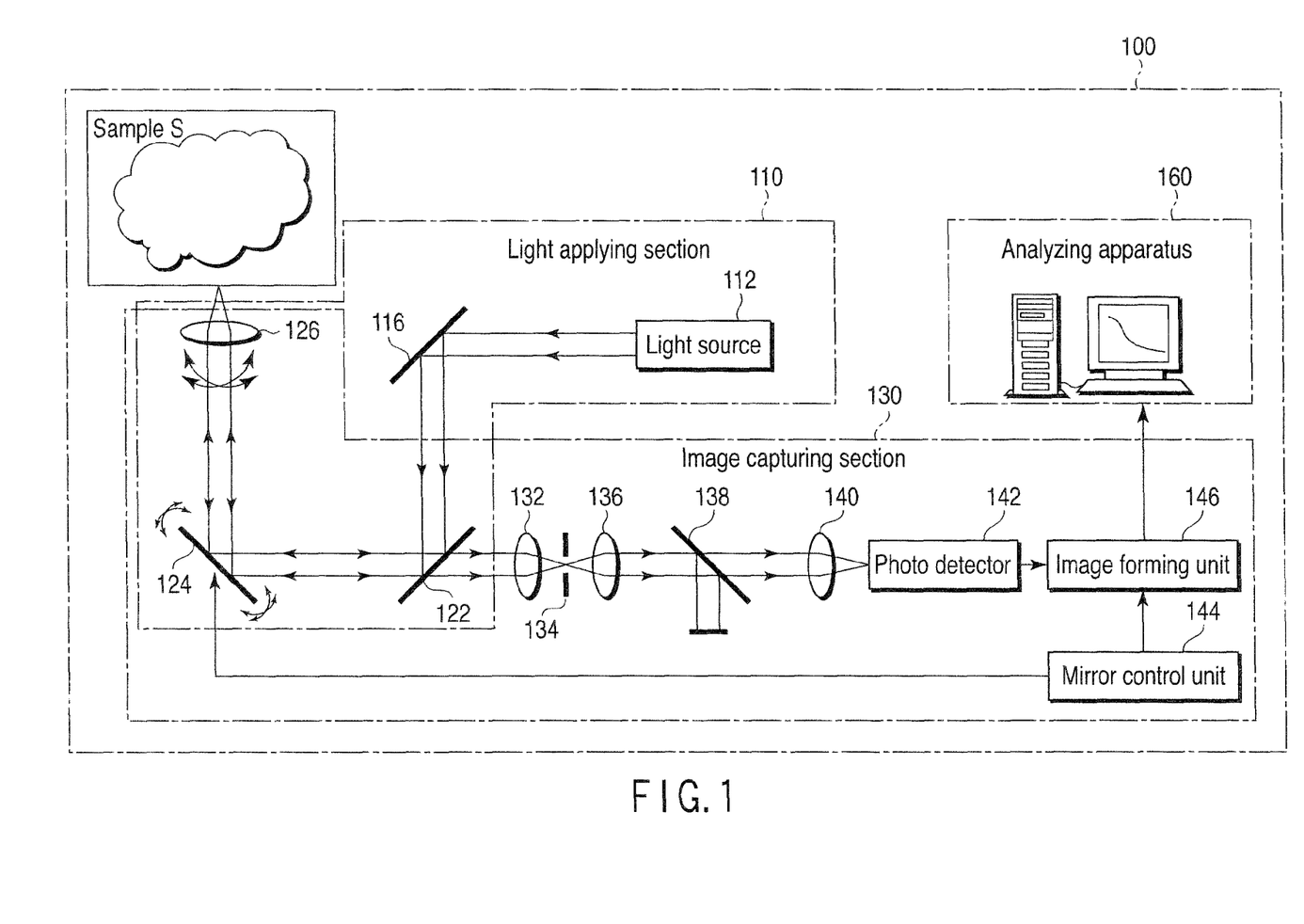
FIG. 1 schematically shows an optical signal analyzing apparatus according to a first embodiment of the present invention.

FIG. 1 schematically shows an optical signal analyzing system according to a first embodiment of the present invention. As shown in FIG. 1, an optical signal analyzing system 100 includes a light applying section 110 to apply excitation light to a sample S, an image capturing section 130 to repetitively capture fluorescent images of the sample S at predetermined time intervals, and an analyzing apparatus 160 to perform an optical signal analysis for the fluorescent images captured by the image capturing section 130.

The light applying section 110 includes a light source 112, a mirror 116, a dichroic mirror 122, a galvanometer mirror 124, and an objective lens 126. The light source 112 emits the excitation light for exciting fluorescent dyes contained in the sample S to cause light (fluorescent light) to be emitted from the sample S. The mirror 116 reflects the excitation light emitted from the light source 112 toward the dichroic mirror 122. The dichroic mirror 122 reflects the excitation light toward the galvanometer mirror 124, and transmits the fluorescent light emitted from the sample S. The galvanometer mirror 124 reflects the excitation light toward the objective lens 126, and also changes the direction of the reflection. The objective lens 126 converges the excitation light to apply it to a measurement point in the sample S, and also takes in light from the measurement point in the sample S.

The image capturing section 130 shares the objective lens 126, the galvanometer mirror 124, and the dichroic mirror 122 with the light applying section 110. The image capturing section 130 further includes a converging lens 132, a pin hole 134, a collimating lens 136, a fluorescence filter 138, a converging lens 140, a photo detector 142, a mirror control unit 144, and an image forming unit 146. The converging lens 132 converges the light transmitted through the dichroic mirror 122. The pin hole 134 is disposed at the focus of the converging lens 132. That is, the pin hole 134 is located in conjugation with the measurement point in the sample S, so as to selectively pass the light from the measurement point. The collimating lens 136 collimates the light passed through the pin hole 134. The fluorescence filter 138 selectively transmits the fluorescent light emitted from the sample S alone. The converging lens 140 converges the fluorescent light that has passed through the fluorescence filter 138. The converging lens 140 cooperates with the collimating lens 136 to project an image of the pin hole 134 onto the photo detector 142. The photo detector 142 outputs a signal corresponding to the intensity of the incident light. That is, the photo detector 142 outputs a fluctuation signal corresponding to the fluctuation of the light from the measurement point in the sample S. The mirror control unit 144 controls the galvanometer mirror 124 so as to raster-scanned the application position of the excitation light over a predetermined region of the sample S. The image forming unit 146 forms a fluorescent image of the predetermined region of the sample S from information on the application position of the excitation light input from the mirror control unit 144 and the output signal of the photo detector 142.

The analyzing apparatus 160 is comprised of, for example, a personal computer. The analyzing apparatus 160 performs the following operations: capture and display of the whole image of the sample S, waiting for the input of specification of an observation region and settings for a minimum delay time and a maximum delay time, selection of a measurement point and determination of the position of the measurement point, analysis (calculation of a pseudo number of molecules), and so on.

Figure 2:
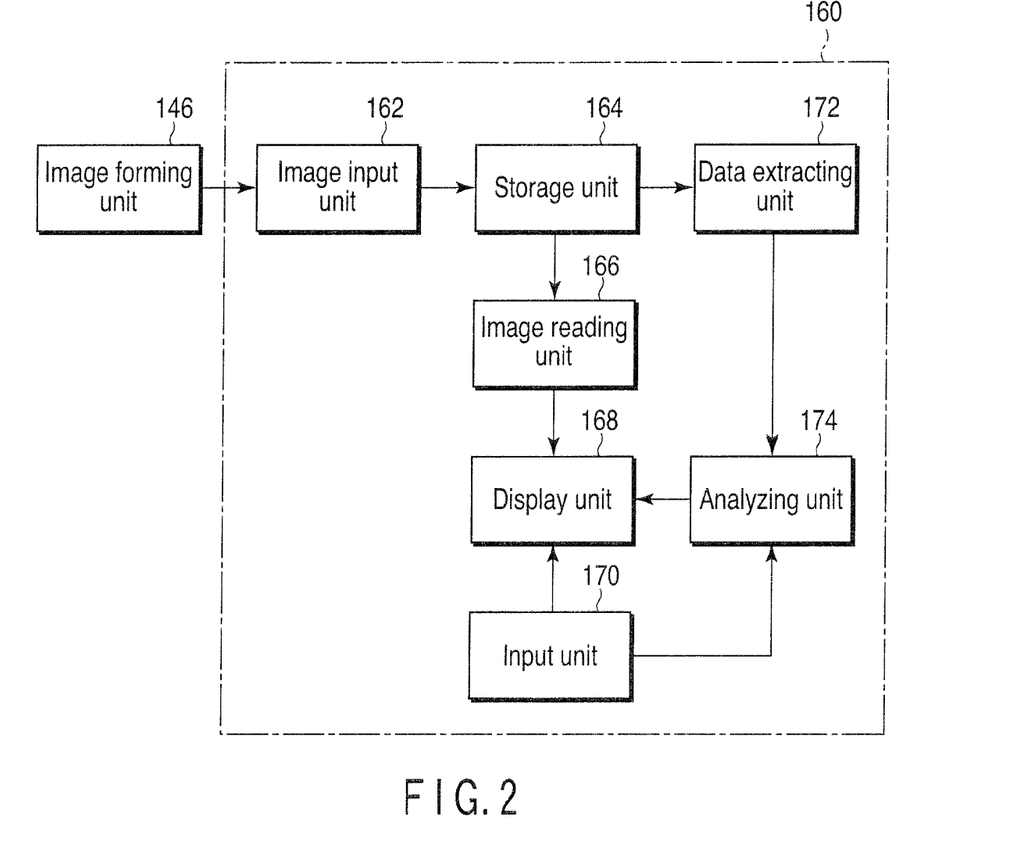
FIG. 2 is a function block diagram of a control unit shown in FIG. 1.

A function block of the analyzing apparatus shown in FIG. 1 is shown in FIG. 2. As shown in FIG. 2, the analyzing apparatus 160 includes an image input unit 162, a storage unit 164, an image reading unit 166, a display unit 168, an input unit 170, a data extracting unit 172, and an analyzing unit 174. The analyzing apparatus 160 is composed of, for example, a personal computer. A plurality of fluorescent images repetitively captured by the image capturing section 130 at predetermined time intervals are input to the image input unit 162. The storage unit 164 stores data on the plurality of fluorescent images input to the image input unit 162. The image reading unit 166 reads at least one of the plurality of fluorescent images stored in the storage unit 164. The display unit 168 displays the fluorescent image read by the image reading unit 166. The input unit 170, which includes, for example, a mouse and a keyboard, cooperates with the display unit 168 to form a GUI. This GUI is used by an operator to specify a desired region targeted for an optical signal analysis on the fluorescent image displayed on the display unit 168. The data extracting unit 172 extracts, for each of the fluorescent images, data on fluorescence intensities in desired regions on the plurality of fluorescent images from the data on the plurality of fluorescent images stored in the storage unit 164. The analyzing unit 174 calculates a correlation and a photon counting histogram for the desired region by use of the data on the fluorescence intensities extracted by the data extracting unit 172. Moreover, the display unit 168 displays an analytic result (the correlation and the photon counting histogram) by the analyzing unit 174, and the GUI composed of the display unit 168 and the input unit 170 is used to specify the way of displaying the analytic result.

In FIG. 1, the excitation light emitted from the light source 112 is applied to the measurement point in the sample S through the mirror 116, the dichroic mirror 122, the galvanometer mirror 124, and the objective lens 126. The measurement point to which the excitation light is applied is raster-scanned by the galvanometer mirror 124. The sample S that has received the excitation light emits fluorescent light from the measurement point. The light (including, for example, undesired reflected light in addition to the fluorescent light) from the sample S reaches the pin hole 134 through the objective lens 126, the galvanometer mirror 124, the dichroic mirror 122, and the converging lens 132. Since the pin hole 134 is located in conjugation with the measurement point, the only light from the measurement point in the sample S passes through the pin hole 134. The light that has passed through the pin hole 134, that is, the light from the measurement point in the sample S reaches the fluorescence filter 138 through the collimating lens 136, and the only fluorescent light emitted from the measurement point in the sample S passes through the fluorescence filter 138. The fluorescent light that has passed through the fluorescence filter 138 enters the photo detector 142 through the converging lens 140. The photo detector 142 outputs, to the image forming unit 146, a signal corresponding to the intensity of the fluorescent light emitted from the measurement point in the sample S. From information on the application position of the excitation light input from the mirror control unit 144 and the output signal of the photo detector 142, the image forming unit 146 forms a fluorescent image composed of the distributions of the intensities of the fluorescent light emitted from the sample S in response to the application of the excitation light. The fluorescent image is input to the analyzing apparatus 160 and analyzed.

In the present embodiment, first, the excitation light is successively applied to different parts of the sample S by the galvanometer mirror 124 to capture one fluorescent image. Then, without ending the fluorescent image collection with the capture of one fluorescent image, the second and third fluorescent images and so forth are repeatedly captured at predetermined time intervals under the same conditions and procedure as described above to capture a plurality of fluorescent images. That is, the plurality of fluorescent images are obtained by repetitively scanning the same region of the same sample in a similar order. Thus, information on the change of the fluorescence intensities in the same desired region over time is obtained, by extraction for each of the fluorescent images, from the stored data on the plurality of fluorescent images.

The captured data on the plurality of fluorescent images is input to the image input unit 162 and stored in the storage unit 164. From the data on the plurality of fluorescent images stored in the storage unit 164, data on the fluorescence intensities in the same desired region is extracted, for each of the fluorescent images, by the data extracting unit 172. The extracted data is sent to the analyzing unit 174 to be used for a correlation analysis and a photon counting histogram analysis for the same desired region or used for data reconstruction, a correlation analysis, and a photon counting histogram analysis for the same desired region.

Figure 5:
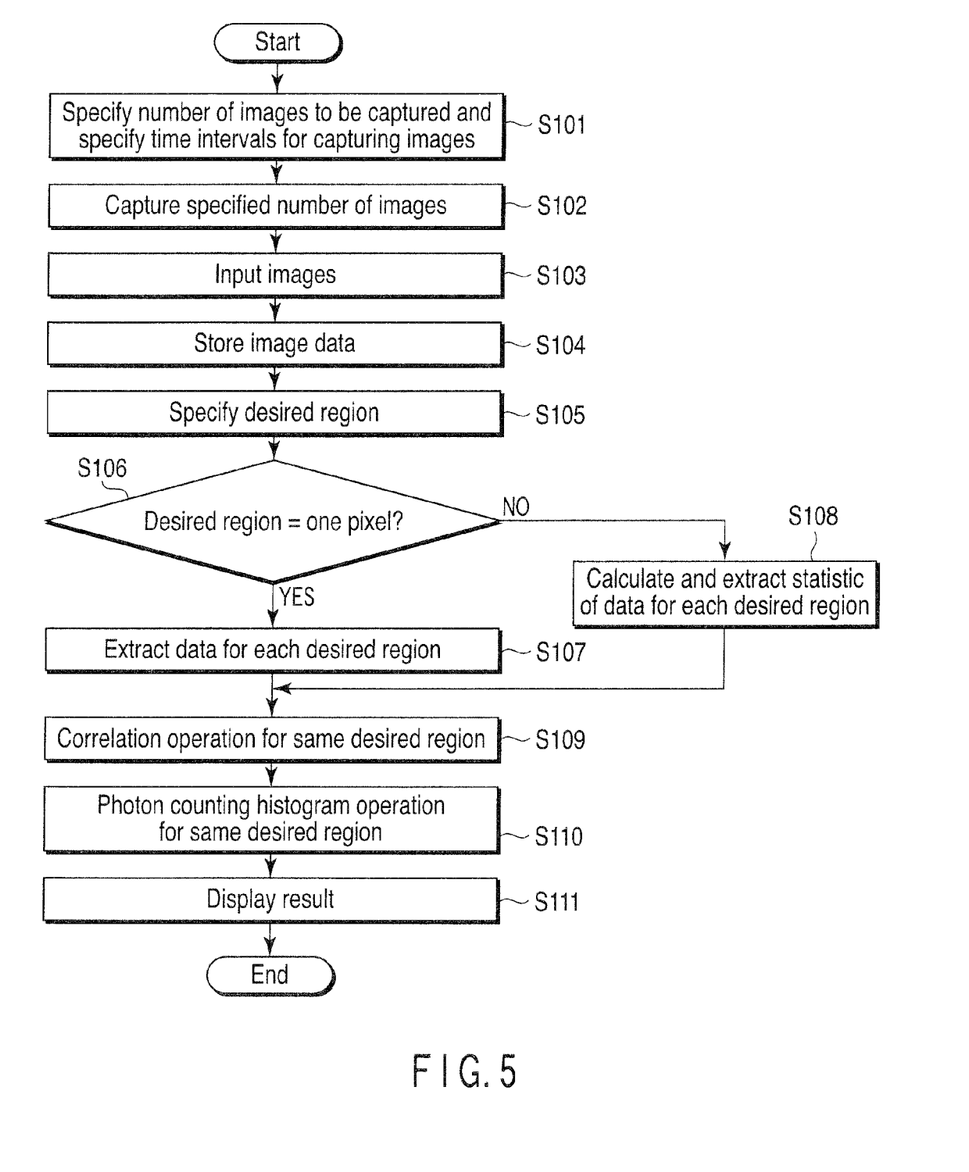
FIG. 5 is a flowchart of an optical signal analysis in the first embodiment.

The optical signal analysis in the present embodiment is described below along with the flowchart in FIG. 5.

[Step S101]

The number of fluorescent images to be captured is specified.

The time intervals (predetermined time intervals) for capturing fluorescent images are set.

Figure 3:
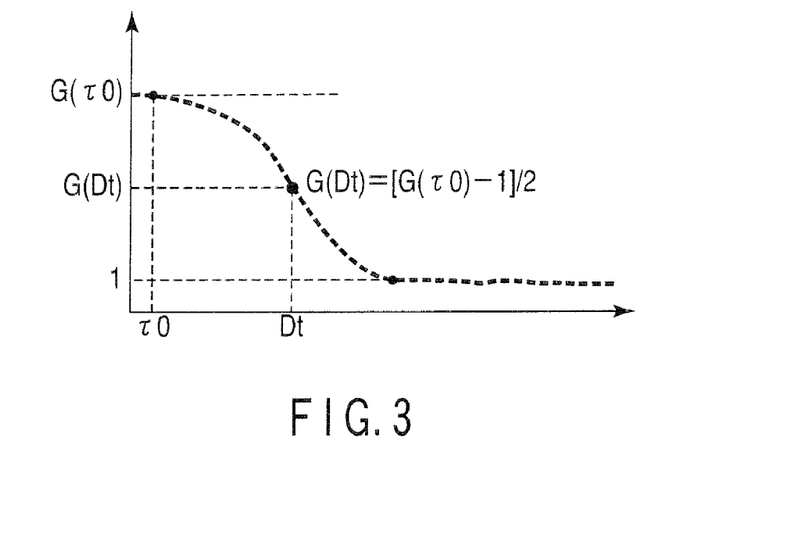
FIG. 3 shows a minimum delay time τ0 and a molecular diffusion time Dt on a correlation curve.

As apparent from FIG. 3, the time interval for capturing the fluorescent image corresponds to a delay time $\tau 0$ of a minimum plot point of a correlation curve. A molecular diffusion time Dt of the sample S can be estimated from $G(Dt) \approx [G(\tau 0)-1]/2$. Therefore, when $\tau 0 > Dt$, it is impossible to estimate Dt from the drawn correlation curve, and an error resulting from fitting is great. Moreover, the molecular diffusion time Dt varies sample by sample. Thus, the time interval for capturing the fluorescent image is set to be shorter than the shortest molecular diffusion time Dt of the sample to be obtained by an analysis.

[Step S102]

Figure 4:
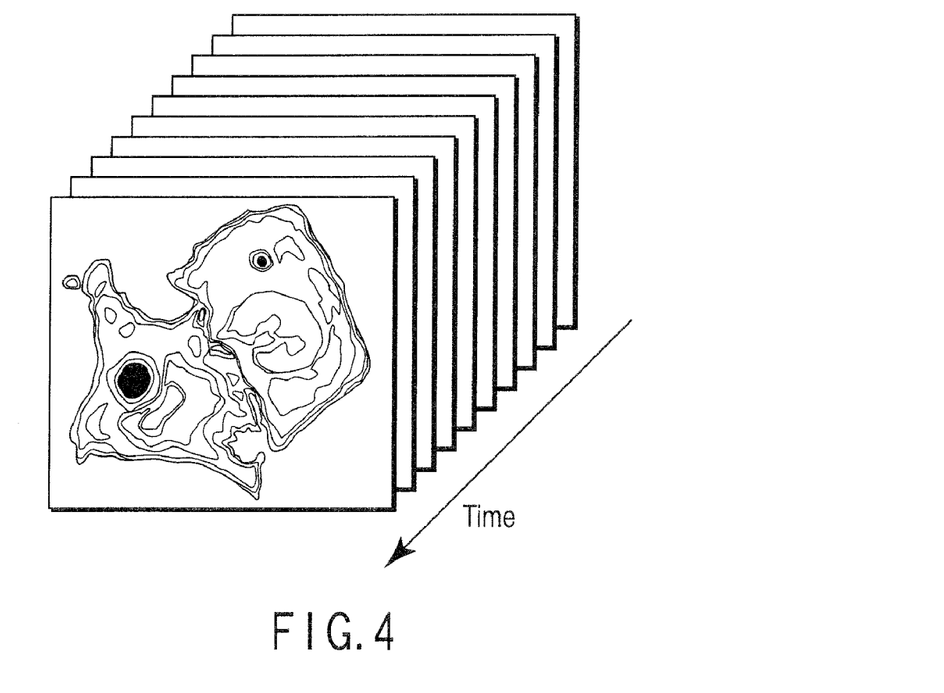
FIG. 4 schematically shows a plurality of fluorescent images captured at predetermined time intervals.

Fluorescent images of the same region in the sample are repetitively captured at the predetermined time intervals. The plurality of fluorescent images captured at the predetermined time intervals are schematically shown in FIG. 4.

[Step S103]

The plurality of captured fluorescent images are input to the image input unit 162.

[Step S104]

Data on the plurality of input fluorescent images is stored in the storage unit 164.

[Step S105]

A desired region (a pixel region including a single pixel or a pixel region including a plurality of adjacent pixels) in the sample to be correlationally analyzed is specified.

[Step S106]

Whether the desired region is the pixel region including a single pixel is judged. If yes, the flow moves to step S107. If no, the flow moves to step S108.

[Steps S106→S107→S109→S110]

If the desired region is the pixel region including a single pixel, then, in step S107, data on fluorescence intensities in the specified desired region is extracted, for each of the fluorescent images, from the data on the plurality of input fluorescent images stored in the storage unit 164.

In step S109, the number of molecules and a diffusion time are analyzed and evaluated by, for example, a correlation operation and fitting with regard to the extracted data on the fluorescence intensities in the desired region.

An equation for an autocorrelation analysis at a measurement point P is represented by Equation (1):

$$G(\tau) = \frac{\left(\sum D(t)D(t+\tau)\right) * N}{\left(\sum D(t)\right)^2} \quad (1)$$

wherein D is the data for a desired region P, and N is the total number of data.

Furthermore, in step S110, a photon counting histogram analyzing method is applied to the extracted data on the fluorescence intensities in the desired region.

[Steps S106→S108→S109→S110]

If the desired region is not the pixel region including a single pixel, that is, if the desired region is the pixel region including a plurality of adjacent pixels, then, in step S108, a statistic of the data on the fluorescence intensities in the pixel region, such as one of an integrated value, an average value, a maximum value, a minimum value, a relative difference, and an absolute difference, is calculated for each of the fluorescent images from the stored data on the plurality of fluorescent images.

Furthermore, data for the specified same desired region (pixel region) is extracted from each of the results of the reconstruction of the plurality of data.

Using the results of the reconstruction of the plurality of data, the number of molecules and the diffusion time are analyzed and evaluated in step S109 by, for example, a correlation operation and fitting with regard to the same desired region (pixel region).

Using the results of the reconstruction of the plurality of data, the photon counting histogram analyzing method is applied to the same desired region (pixel region) in step S110.

[Step S111]

Figure 6:
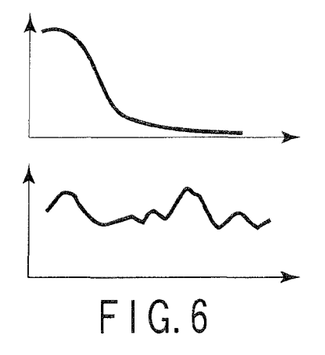
FIG. 6 shows graphs of an analytic result.
Figure 7:
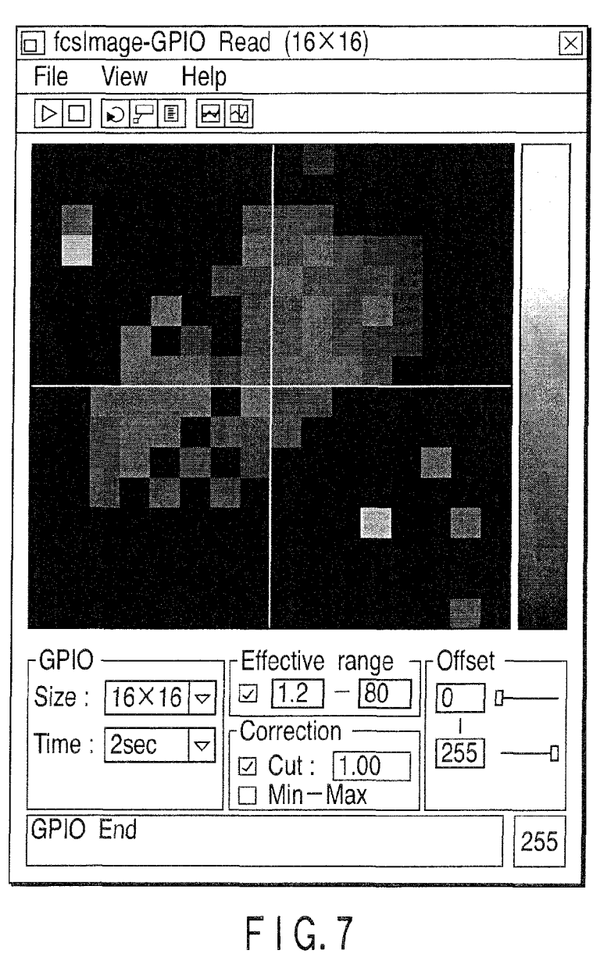
FIG. 7 shows a luminance value of the analytic result.
Figure 8:
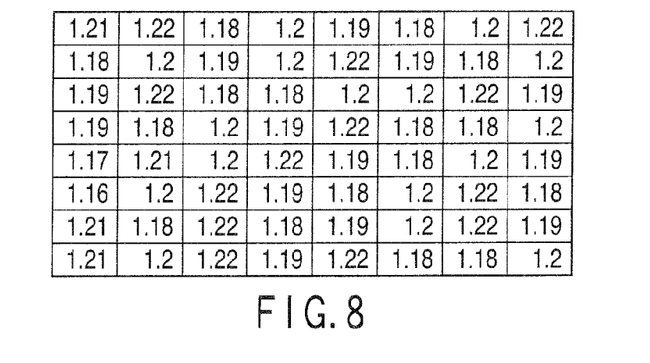
FIG. 8 shows a table of the analytic result.
Figure 9:
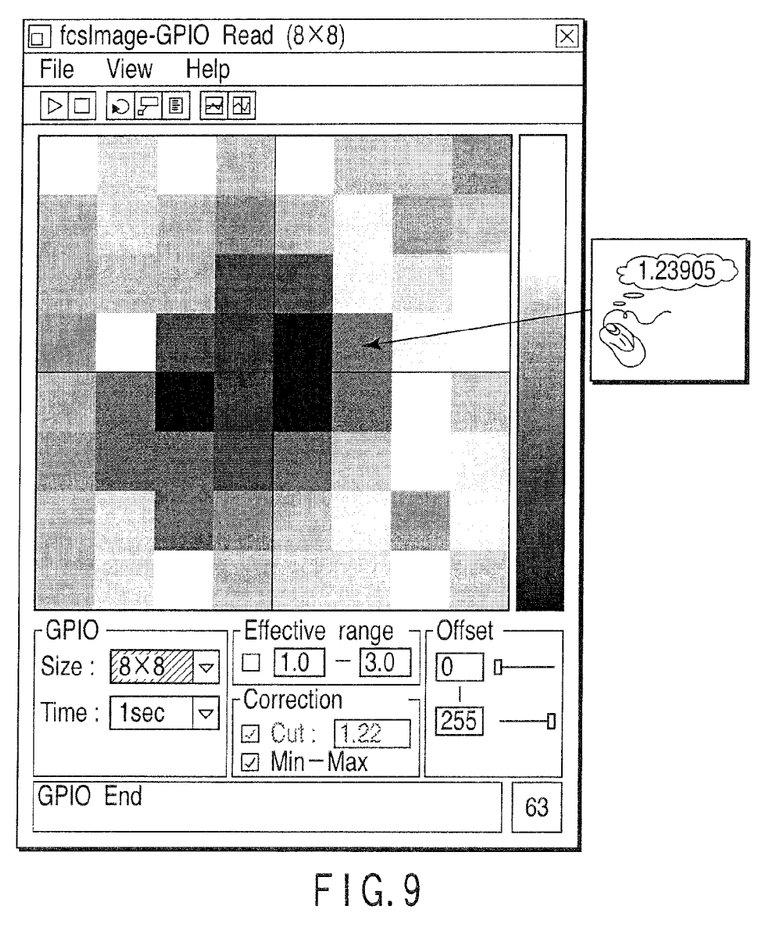
FIG. 9 shows a pin-point display of a numerical value of the analytic result.

The calculation result in each step is displayed on the display unit 168, for example, as graphs as shown in FIG. 6, or as a luminance value as shown in FIG. 7, or as a table as shown in FIG. 8, or as a pin-point displayed numerical value as shown in FIG. 9. Preferably, the calculation result should be displayed on the display unit 168 by one or more display manner including the luminance, table, graph, and numerical value.

The upper part of FIG. 6 shows a correlation curve for one desired region, and the lower part of FIG. 6 shows, by a curve, photon counting data or statistics for one desired region at different times. FIG. 7 shows, by a luminance value, the photon counting data or statistics for one desired region at different times. Alternatively, FIG. 7 shows, by the luminance value, statistics or correlation parameters (e.g., the number of molecules) for a plurality of desired parts. FIG. 8 shows, by a table, the photon counting data or statistics for one desired region at different times. Alternatively, FIG. 8 shows, by the table, statistics or correlation parameters (e.g., the number of molecules) for a plurality of desired parts. FIG. 9 shows, by a luminance value, the photon counting data or statistics for one desired region at different times, and also shows its pin-point value as data. Alternatively, FIG. 9 shows, by the luminance value, statistics or correlation parameters (e.g., the number of molecules) for a plurality of desired parts, and also shows their pin-point values as data.

In the present embodiment, data on fluorescence intensities in the same region is extracted from a plurality of fluorescent images captured at predetermined time intervals, and then the number of molecules and the diffusion time are analyzed and evaluated by, for example, a correlation operation and fitting, or the photon counting histogram analyzing method is applied, which enables observing changes over time in, for example, reactions, and interactions made in and out of the sample S or signal transmission within the sample S. Further, analytic results are indicated by the graphs, luminance value, table or pin-point display, which enables observing and evaluating the physical properties of the sample from many perspectives.

Although the analysis from the data on a plurality of fluorescent images has been described here by way of example, the analysis may be performed from the data on a single fluorescent image.

<Second Embodiment>

FCS/FCCS by Extracted Data for Different Desired Regions

The present embodiment provides a technique of an analysis by extracting data at different spatial positions from data for a plurality of fluorescent images of a sample.

An optical signal analyzing system according to the present embodiment is basically the same in configuration as the optical signal analyzing system in the first embodiment. The present embodiment is different in that instead of only extracting data for the same desired region from a plurality of fluorescent images, data for a plurality of specified different desired regions are extracted and correlationally analyzed.

That is, the present embodiment is the same as the first embodiment in the procedure ranging from the capture to storage of a plurality of fluorescent images.

However, the main point in the technique of the present embodiment is that the photon counting histogram analyzing method and a correlation analysis method for different desired regions are applied to the analysis of stored data.

Figure 10:
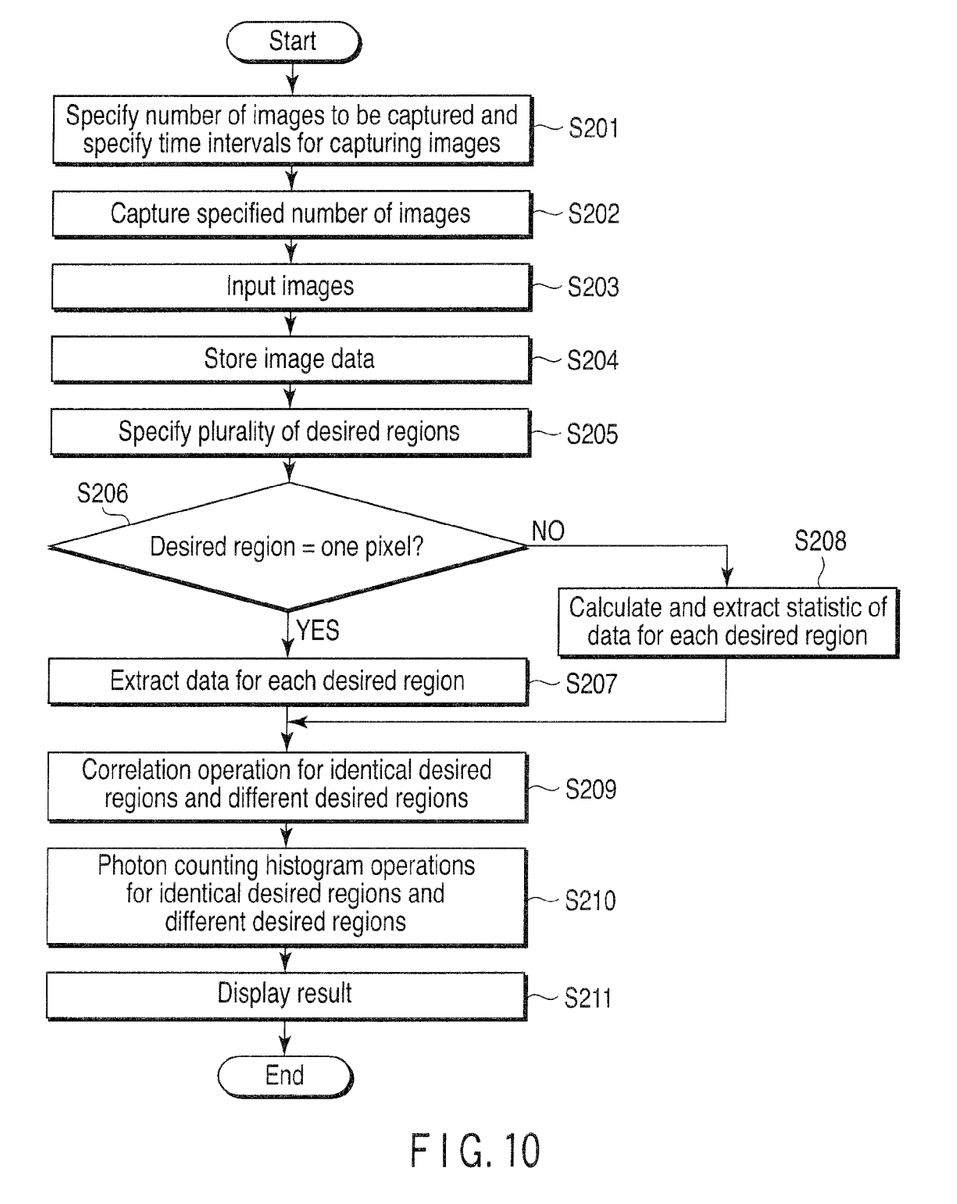
FIG. 10 is a flowchart of an optical signal analysis in a second embodiment.

The optical signal analysis in the present embodiment is described below along with the flowchart in FIG. 10.

[Step S201]

The number of fluorescent images to be captured is specified.

The time intervals (predetermined time intervals) for capturing fluorescent images are set.

[Step S202]
Fluorescent images of a sample at the predetermined time intervals are captured.

[Step S203]
The plurality of captured fluorescent images are input to the image input unit 162.

[Step S204]
Data on the input fluorescent images is stored in the storage unit 164.

[Step S205]
A plurality of desired regions (pixel regions including single pixels or pixel regions including a plurality of adjacent pixels) in the sample to be correlationally analyzed are specified.

[Step S106]
Whether the desired regions are the pixel regions including single pixels is judged. If yes, the flow moves to step S207. If no, the flow moves to step S208.

[Steps S206→S207→S209→S210]
If the desired regions are the pixel regions including single pixels, then, in step S207, data for the plurality of specified desired regions is extracted, for each of the fluorescent images, from the stored data for the plurality of fluorescent images.

In step S209, the number of molecules and the diffusion time are analyzed and evaluated by, for example, a correlation operation and fitting with regard to the extracted data for the identical desired regions or the extracted data for the different desired regions.

Furthermore, in step S210, the photon counting histogram analyzing method is applied to the extracted data for the identical desired regions or the extracted data for the different desired regions.

[Steps S206→S208→S209→S210]
If the plurality of desired regions are not the pixel regions including single pixels, that is, if the plurality of desired regions are the pixel regions including a plurality of adjacent pixels, then, in step S208, statistics of the data for the fluorescence intensities in the plurality of pixel regions, such as statistics of an integrated value, an average value, a maximum value, a minimum value, a difference relative to a certain pixel, and an absolute difference, is calculated in step S208 for each of the fluorescent images from the stored data on the plurality of fluorescent images.

Furthermore, data on the plurality of specified identical desired regions (pixel regions) are extracted from the results of the reconstruction of the plurality of data.

Using the results of the reconstruction of the plurality of data, the number of molecules and the diffusion time are analyzed and evaluated in step S209 by, for example, a correlation operation and fitting with regard to the extracted data for the identical desired regions or the different desired regions.

Equation (1) is used for the identical desired regions and Equation (2) is used for the different desired regions in order to correlationally analyze these regions.

$$G(\tau) = \frac{\left(\sum D_1(t)D_2(t+\tau)\right)*N_{12}}{\left(\sum D_1(t)\right)\left(\sum D_2(t)\right)} \quad (2)$$

wherein $D_1$ is the data for a desired region $P_1$, $D_2$ is the data for a desired region $P_2$, and $N_{12}$ is smaller one of the numbers of data for $D_1$ and $D_2$.

Using the results of the reconstruction of the plurality of data, the photon counting histogram analyzing method is applied in step S210 to the extracted data for the identical desired regions or the different desired regions.

[Step S211]
The calculation result in each step is displayed on the display unit 168, for example, as graphs as shown in FIG. 6, or as an image representing by a luminance value as shown in FIG. 7, or as a table as shown in FIG. 8, or as a pin-point displayed numerical value as shown in FIG. 9. Preferably, the calculation result should be displayed on the display unit 168 by one or more display manner including the luminance, table, graph, and numerical value.

In the present embodiment, data on fluorescence intensities in the same region is extracted from a plurality of fluorescent images captured at predetermined time intervals, and then the number of molecules and the diffusion time are analyzed and evaluated by, for example, a correlation operation and fitting, or the photon counting histogram analyzing method is applied, which enables observing changes over time in, for example, reactions and interactions made in and out of the sample S or signal transmission within the sample S. Further, analytic results are indicated by the graph, luminance values, table or pin-point display, which enables observing and evaluating the physical properties of the sample from many perspectives.

Although the analysis from the data on a plurality of fluorescent images has been described here by way of example, the analysis may be performed from the data on a single fluorescent image.

While the embodiments of the present invention have been described above with reference to the drawings, the present invention is not limited to these embodiments, and various modifications or alterations may be made without departing from the spirit thereof.

In the embodiments described above, the fluorescent image is formed by the distributions of the intensities of the fluorescent light emitted from the sample in response to the application of the excitation light. However, the fluorescent image may be obtained by a laser scanning microscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A fluorescent signal analyzing apparatus comprising:
   an image input unit to which at least one fluorescent image of a sample is input;
   a storage unit to store data on the at least one fluorescent image input to the image input unit;
   an extracting unit to extract, for each of the fluorescent images, data on a fluorescence intensity in a desired region on the at least one fluorescent image from the data on the at least one fluorescent image stored in the storage unit; and
   an analyzing unit to reconstruct data and to calculate at least one of a correlation and a photon counting histogram for the desired region by use of the data on the fluorescence intensity, wherein a plurality of fluorescent images of the sample repetitively captured at predetermined time intervals are input to the image input unit; the storage unit stores data on the plurality of fluorescent images; and the extracting unit extracts, for each of the fluorescent images, data on fluorescence intensities in desired regions on the plurality of fluorescent images from the data on the plurality of fluorescent images stored in the storage unit.

2. The fluorescent signal analyzing apparatus according to claim 1, wherein the desired region is a pixel region including a single pixel.

3. The fluorescent signal analyzing apparatus according to claim 1, wherein the desired region is a pixel region including a plurality of pixels.

4. The fluorescent signal analyzing apparatus according to claim 3, wherein the data on the fluorescence intensities is a statistic of the fluorescence intensities of the plurality of pixels.

5. The fluorescent signal analyzing apparatus according to claim 4, wherein the statistic is one of an integrated value, an average value, a maximum value, a minimum value, a relative difference, and an absolute difference of the fluorescence intensities of the plurality of pixels.

6. The fluorescent signal analyzing apparatus according to claim 1, wherein the fluorescent image is composed of distributions of the fluorescence intensities.

7. The fluorescent signal analyzing apparatus according to claim 1, wherein the analyzing unit calculates a diffusion time by further using the predetermined time intervals.

8. The fluorescent signal analyzing apparatus according to claim 1, further comprising a specifying unit to specify the desired region.

9. The fluorescent signal analyzing apparatus according to claim 1, further comprising a display unit to display, by at least one of luminance, a table, a graph, and a numerical value, a result calculated by the analyzing unit.

10. The fluorescent signal analyzing apparatus according to claim 1, further comprising:
    a display unit to display at least one of the at least one of the fluorescent images stored in the storage unit; and
    a region specifying unit to specify the desired region on the fluorescent image displayed on the display unit.

11. A fluorescent signal analyzing method comprising:
    storing data on at least one fluorescent image of a sample;
    extracting, for each of the fluorescent images, data on a fluorescence intensity in a desired region on the at least one fluorescent image from the stored data on the at least one fluorescent image; and
    reconstructing data and calculating at least one of a correlation and a photon counting histogram for the desired region by use of the extracted data on the fluorescence intensity, wherein the storing includes storing data on a plurality of fluorescent images of the sample repetitively captured at predetermined time intervals, and the extracting includes extracting, for each of the fluorescent images, data on fluorescence intensities in desired regions on the plurality of fluorescent images from the stored data on the plurality of fluorescent images.

12. The fluorescent signal analyzing method according to claim 11, wherein the desired region is a pixel region including a single pixel.

13. The fluorescent signal analyzing method according to claim 11, wherein the desired region is a pixel region including a plurality of pixels.

14. The fluorescent signal analyzing method according to claim 13, wherein the data on the fluorescence intensities is a statistic of the fluorescence intensities of the plurality of pixels.

15. The fluorescent signal analyzing method according to claim 14, wherein the statistic is one of an integrated value, an average value, a maximum value, a minimum value, a relative difference and an absolute difference of the fluorescence intensities of the plurality of pixels.

16. The fluorescent signal analyzing method according to claim 11, wherein the fluorescent image is composed of distributions of the intensities of fluorescent light emitted from the sample in response to the application of excitation light.

17. The fluorescent signal analyzing method according to claim 11, further comprising calculating a diffusion time by using the predetermined time intervals.

18. The fluorescent signal analyzing method according to claim 11, further comprising displaying an analytic result by at least one of luminance, a table, a graph and a numerical value.

19. The fluorescent signal analyzing method according to claim 11, further comprising:
    displaying at least one of the at least one of the fluorescent images; and
    specifying the desired region on the displayed fluorescent image.

* * * * *